United States Patent [19]

Moore, Jr. et al.

[11] Patent Number: 5,498,395
[45] Date of Patent: Mar. 12, 1996

[54] LIQUID COLLECTION AND SEPERATION APPARATUS

[76] Inventors: Glenn A. Moore, Jr., 1473 Dartmouth Dr., Clearwater, Fla. 34616; Christopher J. Mannari, 12760 Indian Rocks Rd. #113, Largo, Fla. 34644

[21] Appl. No.: 120,811

[22] Filed: Sep. 14, 1993

[51] Int. Cl.⁶ .................................................. B01L 3/02
[52] U.S. Cl. .................... 422/100; 422/99; 422/102; 422/104; 141/331; 141/237
[58] Field of Search ............... 141/331 X, 332, 141/340, 333, 237 X; 422/99, 100, 101, 104, 102

[56] References Cited

U.S. PATENT DOCUMENTS

| | | | |
|---|---|---|---|
| 530,746 | 12/1894 | Burke | 141/331 |
| 2,056,191 | 10/1936 | Peltz | 141/237 |
| 3,693,673 | 9/1972 | Oates | 141/237 |
| 3,732,902 | 5/1973 | Oates | 141/237 |
| 4,079,761 | 3/1978 | Herbst, Sr. | 141/198 |
| 4,335,730 | 6/1982 | Griffin | 128/760 |
| 4,492,258 | 1/1985 | Lichtenstein et al. | 141/1 |
| 4,494,581 | 1/1985 | Gordon | 141/1 |
| 4,830,068 | 5/1989 | Langenhahn et al. | 141/266 |
| 4,896,746 | 1/1990 | Desjardins | 184/92 |
| 4,981,144 | 1/1991 | Carels, Jr. | 128/760 |
| 5,043,082 | 8/1991 | Hermann, Jr. et al. | 210/772 |
| 5,123,458 | 6/1992 | Collard | 141/1 |

*Primary Examiner*—James C. Housel
*Assistant Examiner*—Long V. Le
*Attorney, Agent, or Firm*—Joseph C. Mason, Jr.; Ronald E. Smith

[57] ABSTRACT

A collection and separation funnel for urine, other body fluids, or environmental samples has dual downspouts so that liquid entering the funnel flows in part down a first downspout and in part down a second downspout. A centrifuge tube is releasably connected to each downspout to receive the liquid. This enables detachment of the centrifuge tubes for delivery to different laboratories. A stand releasably receives the lowermost ends of each centrifuge tube so that the device is free standing and need not be held at the time of liquid collection. A lid is provided for the funnel to facilitate its transportation, and individual lids are provided for each centrifuge tube.

4 Claims, 2 Drawing Sheets

LIQUID COLLECTION AND SEPERATION APPARATUS

BACKGROUND OF THE INVENTION

1. Field of the Invention

This invention relates, generally, to devices used for collecting specimens for medical analysis. More particularly, it relates to a urine specimen collecting device that divides the urine into two separate containers at the time of collection.

2. Description of the Prior Art

Urine specimens are routinely collected in small sterile cups if a culture is to be grown or in a nonsterile cup if a urinalysis has been ordered. Thus, whenever a specimen is going to be subjected to culturing by one lab and urinalysis by another lab, the specimen container must be sterile. After collection, a first amount of the collected urine is transferred to a sterile container for culturing and a second amount is transferred to a container that need not be sterile for urinalysis. Typically, the containers to which the urine is transferred are test tubes, also known as centrifuge tubes.

Both transfers of the urine are accomplished by pouring part of the contents of the collection receptacle into the centrifuge tubes. The initial collection receptacle is then discarded; one of the two centrifuge tubes is transported to a microbiology lab for culturing and the other one is transported to a hematology lab for urinalysis.

There are a number of drawbacks to the above-described, widely practiced procedure. For example, the individual transferring the urine from the initial collection container to the centrifuge tubes may spill the urine onto his or her hands and thus suffer exposure to possible disease organisms. Moreover, the handling may introduce contaminating organisms into the specimen, producing false positives when various procedures are performed. Furthermore, when the contents of one cup are poured into two additional cups, still another transfer will be required if the specimen is to be centrifuged.

Thus, there is a need for an improved means for dividing the contents of a urine collection container into two separate containers, and for eliminating an additional step of emptying those separate containers into centrifuge tubes, but at the time the present invention was made, it was not obvious to those of ordinary skill in this art how such improved means could be provided, in view of the prior art when considered as a whole. The absence of an obvious solution to the problem is apparent from the very longstanding practice of following the prior art separation technique described above.

SUMMARY OF THE INVENTION

The very longstanding but heretofore unfulfilled need for an improved urine specimen collection and separation apparatus is now fulfilled.

The invention includes a funnel having a bifurcated downspout, i.e., a pair of downspouts are integrally formed with the narrow end of a funnel and depend therefrom in spaced apart, parallel relation to one another on opposite sides of a divider wall positioned between the respective openings of the downspouts. Each downspout is adapted to snugly but releasably receive the open end of a centrifuge tube so that the urine is divided and flows into both tubes at the time of collection, thereby obviating any further need to perform a separation procedure.

A base for mounting the apparatus in a free standing configuration is provided so that the apparatus need not be held at the time of specimen collection. A lid for the funnel and individual lids for the centrifuge tubes are also provided.

Thus it is clear that the primary object of this invention is to advance the art of urine collection and specimen handling.

A more specific object is to provide an apparatus that accomplishes urine separation into two centrifuge tubes at the time of specimen collection.

Another important object is to provide a specimen-collecting device that is not susceptible to contamination.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
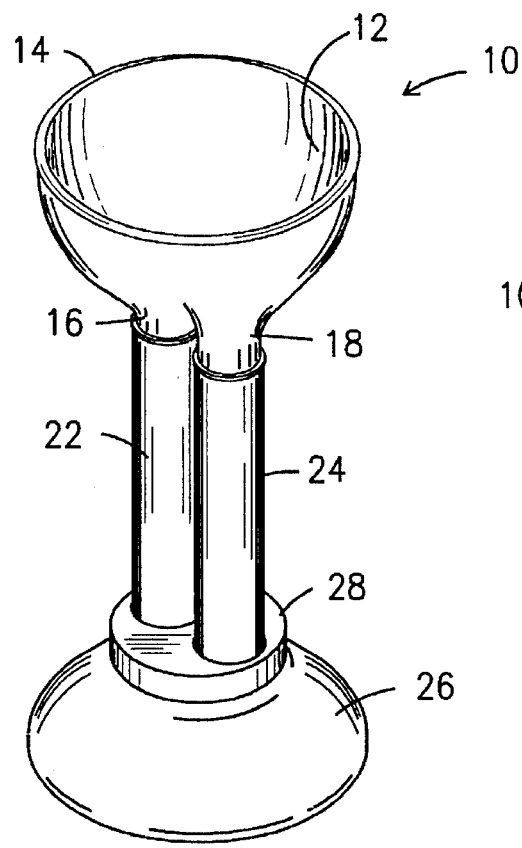
FIG. 1 is a perspective view of the novel apparatus when in its assembled configuration with the funnel lid removed.
Figure 2:
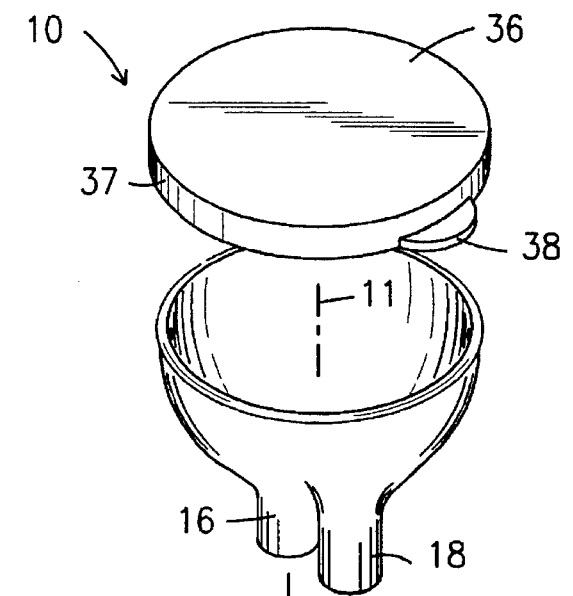
FIG. 2 is an exploded perspective view of the novel apparatus.
Figure 2:
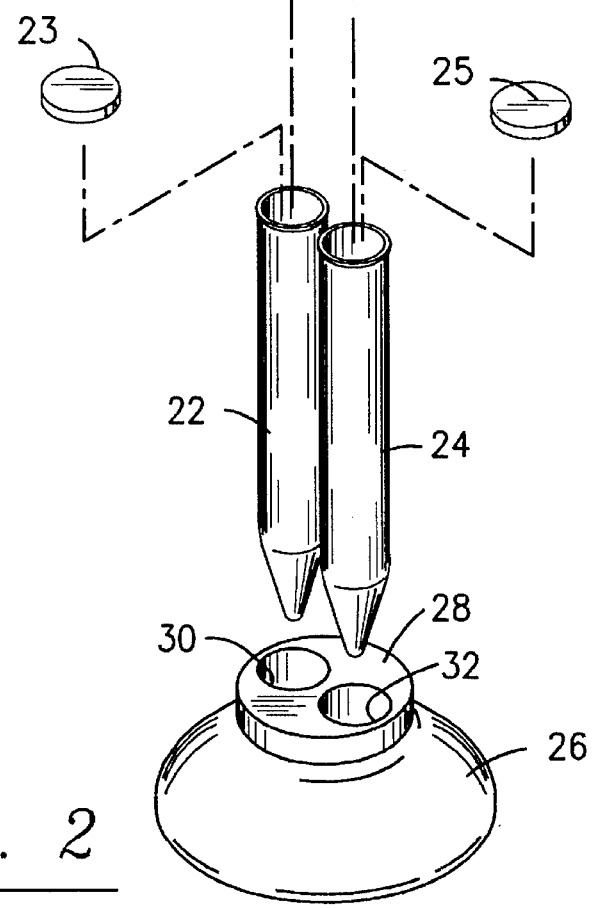
Figure 3:
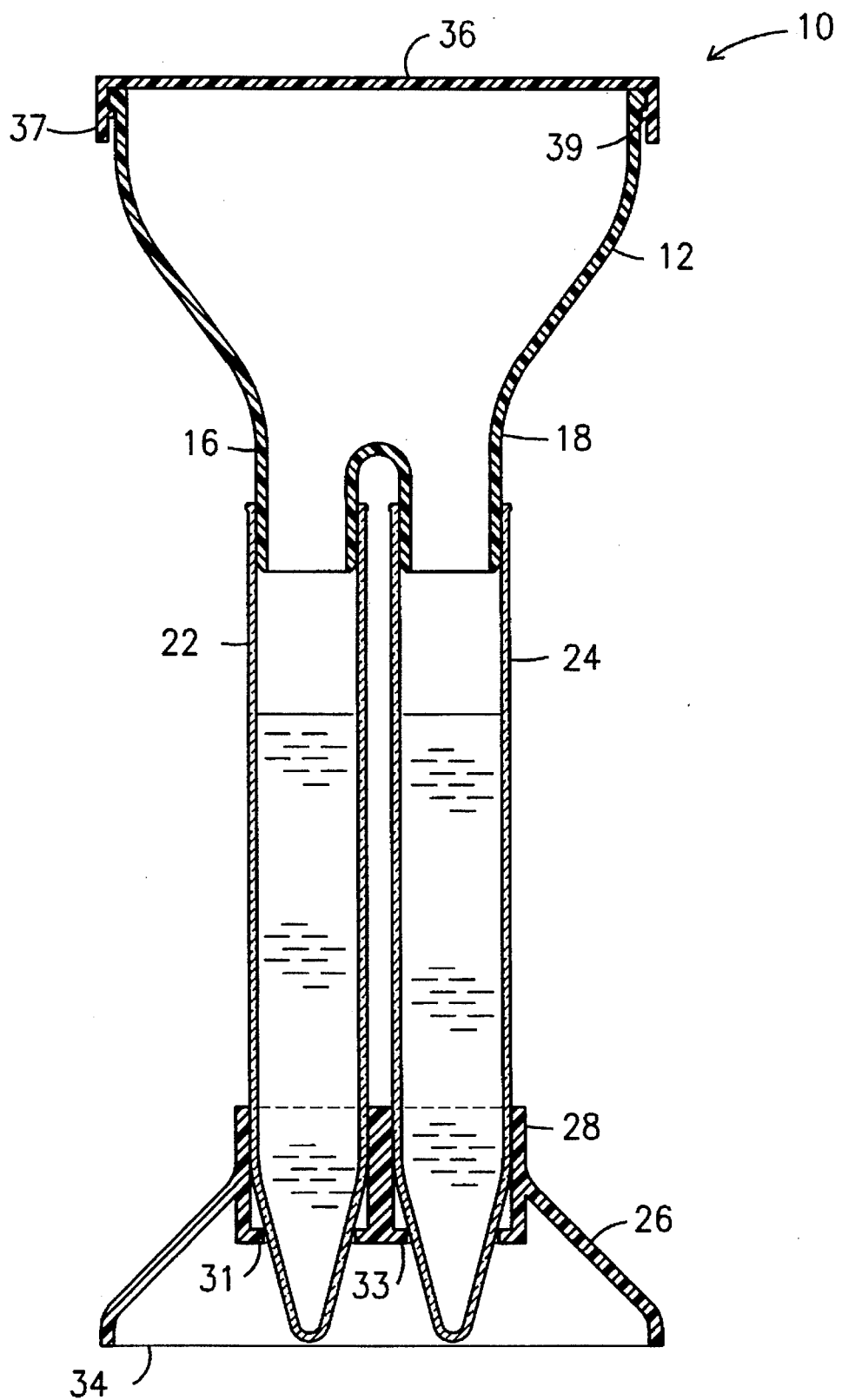
FIG. 3 is a longitudinal sectional view of the device in its FIG. 1 configuration.

Referring now to FIGS. 1–3, it will there be seen that an illustrative embodiment of the invention is denoted as a whole by the reference numeral 10. Reference numeral 11 in FIG. 3 indicates the longitudinal axis of symmetry of apparatus 10.

Specimen divider 10 includes a generally frustoconical, funnel wall 12 having an annular rim 14 and a pair of parallel downspouts 16, 18 that are integrally formed with and which depend from a lowermost, narrow end of wall 12. A divider wall 20 (FIG. 3) is integrally formed with funnel wall 12 and the respective uppermost ends of said downspouts 16, 18 and is preferably of rounded, convex construction as shown so that urine or other liquid falling thereupon will be generally divided into two separate streams that flow into said downspouts 16, 18. A pointed or other nonconvex divider wall is also within the scope of this invention.

The lowermost end of each downspout is slidably and snugly received by the uppermost end of an associated centrifuge tube 22, 24. The reverse construction, where the uppermost ends of the centrifuge tubes would be received within an associated downspout, is also within the scope of this invention.

Note that downspouts 16, 18 share a common diameter, a common length, and are positioned on opposite sides of longitudinal axis of symmetry 11 in equidistantly spaced relation thereto. Note further that divider wall 20 is bisected by longitudinal axis of symmetry 11; thus, both downspouts are adapted to engage a conventional centrifuge tube and both downspouts have a substantially equal chance of receiving liquid deposited into the funnel. Accordingly, the specimen, once collected, need not be handled before its introduction into separate centrifuge tubes and the possibility of contamination is thereby minimized.

Base 26 performs the function of holding the funnel, downspouts, and centrifuge tubes in a free standing configuration so that apparatus 10 need not be hand-held at the time of specimen collection. It includes a central hub 28 having a pair of bores 30, 32 formed therein; each bore receives the lowermost end of a centrifuge tube in the manner depicted in FIG. 3. Note that each bore has a bottom wall 31, 33, that ensures that the ends of the tubes will not extend beyond the plane 34 defined by the bottom of base 26.

As depicted in FIGS. 2 and 3, lid 36 includes depending sidewall 37 that releasably engages annular rim 14 of funnel 12. Rim 14 is provided in the form of an annular bead as best shown in FIG. 3, and a radially inwardly protruding annular ridge 39 is formed on sidewall 37 to form a bead-receiving recess that holds lid 36 against inadvertent removal.

Tab 38 extends radially from said sidewall 37 to facilitate removal of lid 36.

Lids 23 and 25, shown in FIG. 2, may be used to cap each centrifuge tube; they engage the annular bead formed at the rim of each tube in substantially the same way as lid 36 engages rim 14 of the funnel.

Excess urine that collects within funnel 12 is discarded prior to separation of the centrifuge tubes from their respective downspouts. The centrifuges are then slipped off their respective downspouts, and lids 40 are applied thereto. The individual centrifuge tubes are then lifted from their respective bores 30, 32, and routed to the appropriate lab in the absence of contamination or spillage.

The novel apparatus may also be employed to collect specimens other than urine such as other body fluids or environmental samples or the like. Moreover, funnel constructions having more than two downspouts are also within the scope of this invention.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An apparatus for collecting a liquid specimen, comprising:

a funnel wall having a rim at a first end thereof, said rim having a first predetermined diameter;

said funnel wall being exposed to an ambient environment so that it may receive a stream of liquid specimen directed thereinto;

said funnel wall having a pair of openings at a second end thereof, each opening of said pair of openings having a second predetermined diameter less than said first predetermined diameter;

a pair of downspouts formed integrally with each opening of said pair of openings;

each of said downspouts having a free end;

each of said downspouts having a common uniform diameter and being disposed in parallel relation to one another;

said apparatus having a longitudinal axis of symmetry;

each of said downspouts having imperforate sidewalls;

said openings being disposed on opposite sides of said longitudinal axis of symmetry, in equidistant relation thereto;

a divider wall, bisected by said longitudinal axis of symmetry, being disposed between said openings so that at least some of the liquid introduced into the funnel is diverted by said divider wall into both of said openings;

said divider wall being integral with said funnel wall;

a plurality of centrifuge tubes, each having an open end and a closed end, said open end releasably connected to each of said free ends of said downspouts; and a stand for releasably engaging respective closed ends of centrifuge tubes connected to said respective downspouts;

whereby contamination of a liquid specimen is substantially avoided during division of the liquid specimen into separate parts.

2. The apparatus of claim 1, wherein said divider wall has a convex surface.

3. The apparatus of claim 1, further comprising a first removably mounted lid means adapted to engage said rim.

4. The apparatus of claim 1, further comprising a second removably mounted lid means adapted to engage said open end of a centrifuge tube.

\* \* \* \* \*